(12) United States Patent
Westermann et al.

(10) Patent No.: US 6,259,942 B1
(45) Date of Patent: Jul. 10, 2001

(54) METHOD AND APPARATUS FOR RECORDING A THREE-DIMENSIONAL IMAGE OF A BODY PART

(75) Inventors: Birgit Westermann, Schweiz; Rolf Hauser, Bellingen, both of (DE)

(73) Assignee: Surgical Navigation Specialist Inc., Mississauga (CA)

(*) Notice: Subject to any disclaimer, the term of this patent is extended or adjusted under 35 U.S.C. 154(b) by 0 days.

(21) Appl. No.: 09/247,186

(22) Filed: Sep. 25, 1998

(30) Foreign Application Priority Data

Sep. 27, 1997 (EP) .................................................. 97116843

(51) Int. Cl.$^7$ ............................... A61B 6/00; A61B 8/13; A61B 5/05
(52) U.S. Cl. .......................... 600/426; 600/414; 600/425; 378/162
(58) Field of Search .................................... 600/414, 410, 600/425, 427, 429, 595; 606/130; 378/205, 206, 162, 163; 356/247, 248; 324/309, 319

(56) References Cited

U.S. PATENT DOCUMENTS 4,971,060 * 11/1990 Schneider et al. .................. 378/162
5,423,315   6/1995 Margosian et al. .
5,485,493   1/1996 Heuscher et al. .
5,552,605   9/1996 Arata .
5,577,502 * 11/1996 Darrow et al. ........................ 600/410
5,579,358  11/1996 Lin .
5,588,430  12/1996 Bova et al. .
5,828,722  10/1998 Ploetz et al. .
5,954,647 *  9/1999 Bova et al. .......................... 378/205

FOREIGN PATENT DOCUMENTS

3447365 A1    7/1986  (DE) .
0654675 A1    5/1995  (EP) .
0662305 A1    7/1995  (EP) .
0807404 A1   11/1997  (EP) .
 4-226641 *   8/1992  (JP) .
 9625098      8/1996  (WO) .

* cited by examiner

Primary Examiner—Joseph Pelham
(74) Attorney, Agent, or Firm—John R. S. Orange; Orange & Chari

(57) ABSTRACT

While acquiring a tomographic image, the position of patient's head is continuously measured and recorded. For this purpose, several cameras (5) are arranged at the tomograph (1). They measure the position of a reference device (4), which is mounted to the teeth of the patient's upper jaw. Infrared-diodes are arranged on the reference device (4), the position of which is recorded by the cameras (5). This allows to measure the movements of the patient and to compensate for them when generating the tomographic image.

21 Claims, 3 Drawing Sheets

METHOD AND APPARATUS FOR RECORDING A THREE-DIMENSIONAL IMAGE OF A BODY PART

Figure 1:
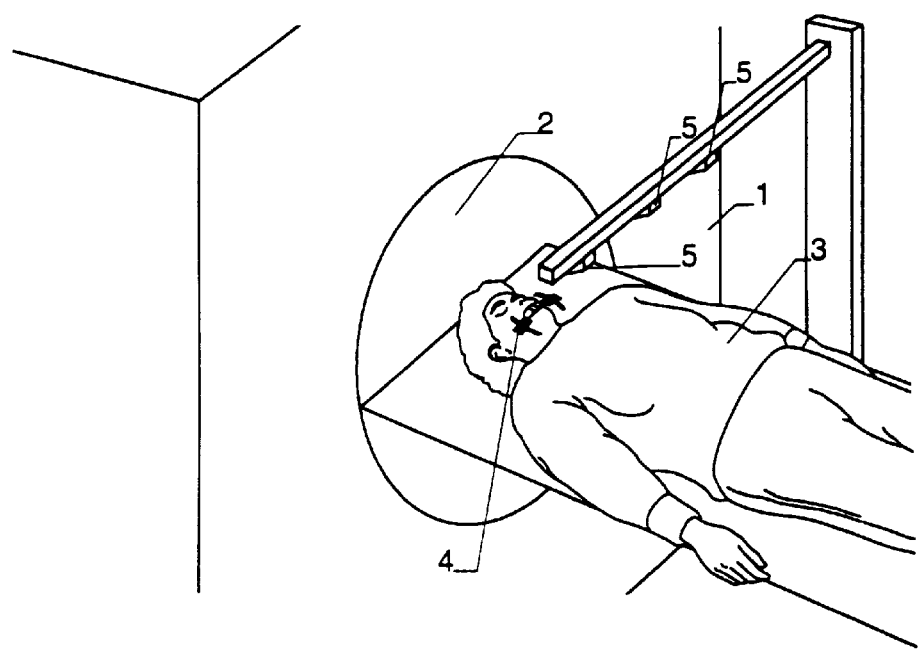

The invention relates to a method and an apparatus for recording a three dimensional image of a part of a patient's body according to the preamble of the independent claims as well as to a reference device for being mounted to a patient's head while using such a method.

Various methods and devices are known for recording three-dimensional images of a part of a patient's body. Three dimensional images of this type are usually generated from a plurality of planar scans and information describing the spatial relation between these scans and/or between the patient and the scans. Known methods are e.g. based on the principles of computer tomography, NMR tomography, ultrasound analysis, positron emission tomography or X-ray techniques. Especially while recording extended areas it is important that the part of the body is fixed in place because movement may affect the quality of the image. However, immobilization of the position of a body part, such as a patient's head, is usually difficult and/or uncomfortable for the patient due to invasive attachments of head rings or frames.

It is therefore an object of the present invention to provide a device and a method of the type mentioned above that obviates these disadvantages at least partially.

This object is met by the independent claims.

By measuring movements, i.e. positional changes, of the body part during image acquisition, it becomes possible to correct the acquired image data. If the patient e.g. moves (especially turns) during acquisition, the image data are corrected such that all scanned images are transformed to the same coordinate system and can be combined with high accuracy.

Preferably, the movements or positional changes are detected optically, e.g. by affixing reference markers to the body part, which are observed by a camera system. However, it is also possible to detect the position of the body part directly be means of suited image processing techniques, i.e. without using reference markers. In any case, an optical position detection is preferred for its simplicity and high immunity to noise. But it is also possible to detect movements and positional changes by other means, e.g. ultrasonic triangulation.

Preferably, a reference device with suited reference marks is mounted to the body part to be measured.

If the measurement is performed on a patient's head, the reference device should be attached to at least one tooth of the patient's upper jaw. Further connections between the head and the reference device are not necessary. The reference device can be affixed to upper jaw by conventional dental impression material or by other means of fixation, such as clamps or dental prostheses for toothless patients.

Preferably, the reference device comprises a mouthpiece, which is non-invasively connected to the upper jaw in the manner described above, as well as a reference member attachable to the mouth piece for being detected by the positional detector. The reference member can be titled in respect to the mouthpiece, which allows to establish an optimum orientation for each recording geometry.

In a preferred embodiment the relation of the reference markers (i.e. the coordinate system of the positional director) in respect to the body part (i.e. the coordinate system of the three-dimensional image or the coordinate system of the imaging system) are stored together with the image. This makes it possible to position the patient later by means of the reference markers.

Figure 2:
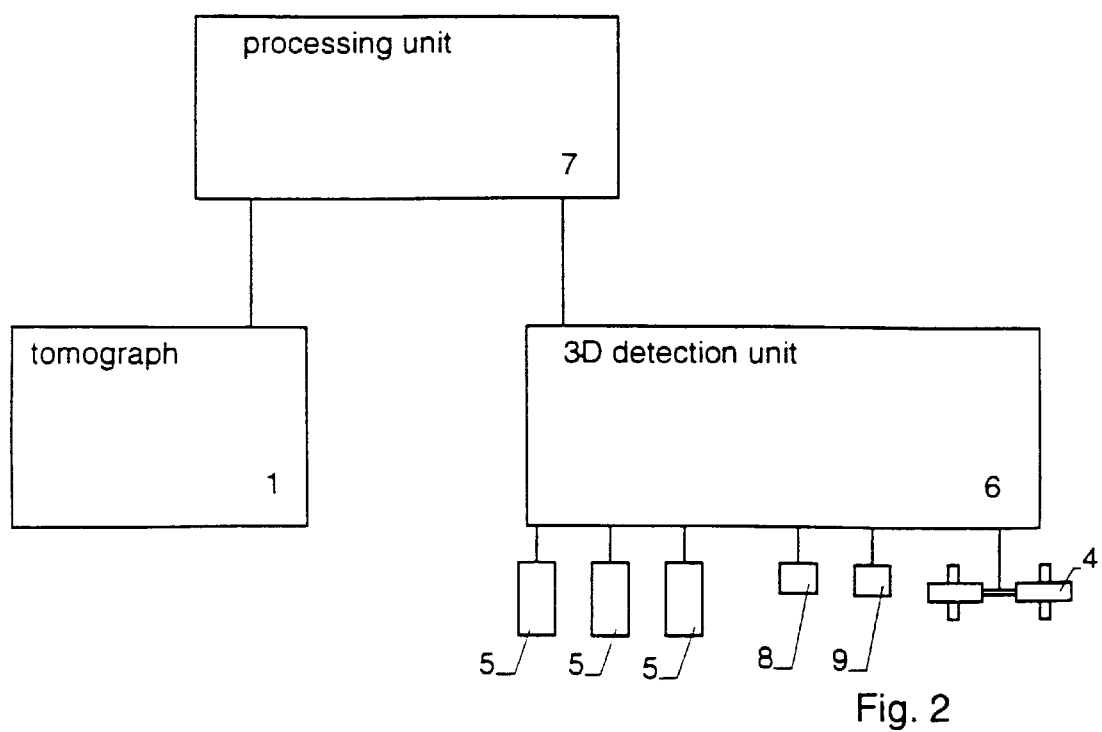
Figure 3:
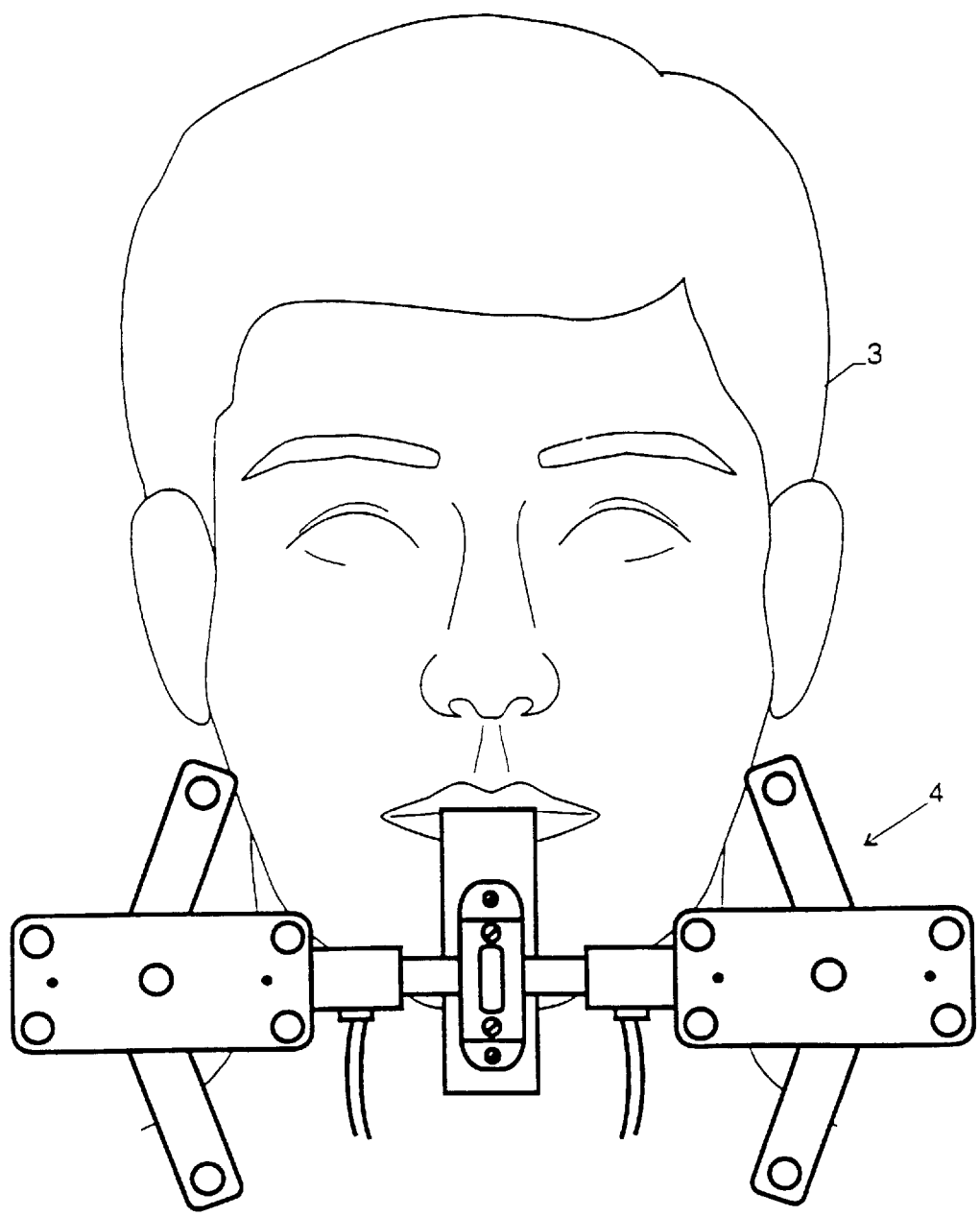
Figure 4:
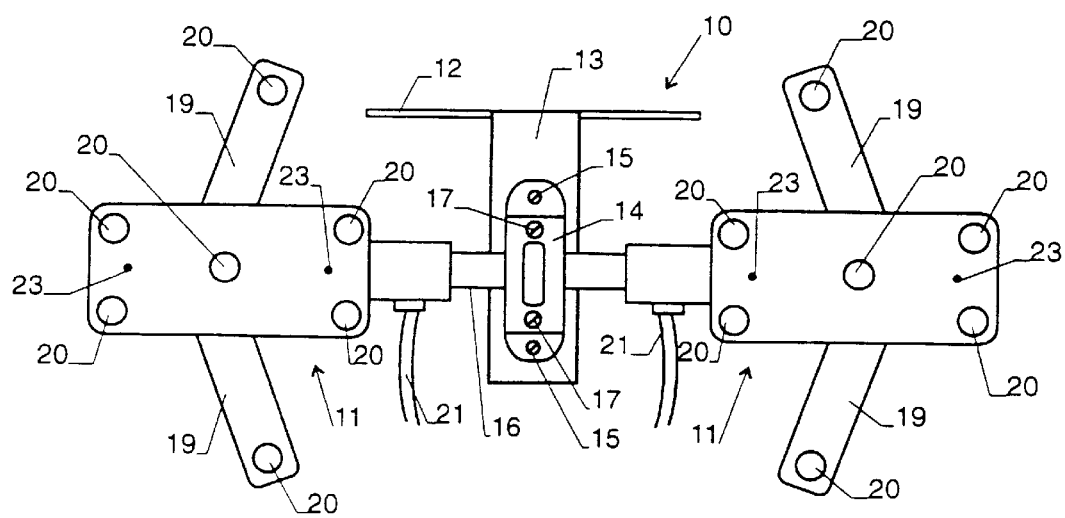

Further advantages, applications and preferred embodiments are described in the dependent claims and the following disclosure of an embodiment with reference to the figures. The figures show:

FIG. 1 a view of a topographic apparatus according to the present invention,

FIG. 2 a block diagram of the apparatus of FIG. 1,

FIG. 3 a reference device according to the invention in the mouth of a patient,

FIG. 4 the reference device of FIG. 3, and

Figure 5:
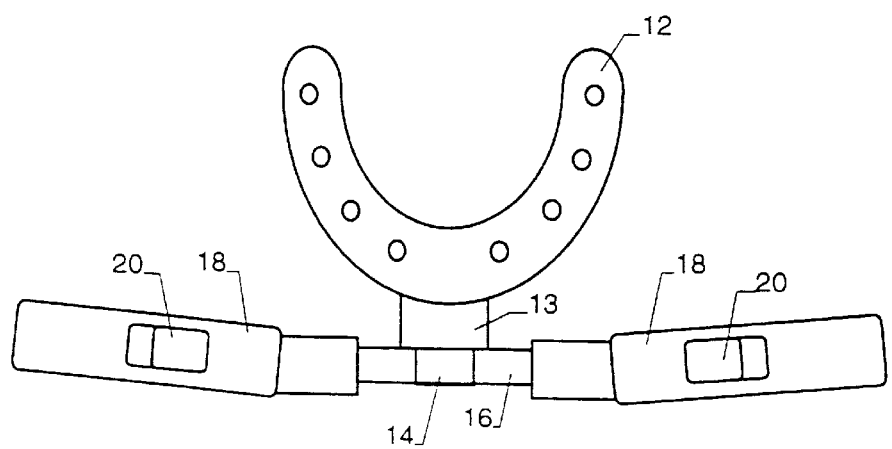

FIG. 5 a view of the device of FIG. 4 perpendicular to the mouth piece.

FIG. 1 shows an application of the invention in a computer tomograph 1. Computer tomograph 1 comprises a measuring zone 2 for receiving the head of the patient 3. As will be described in more detail, the patient 3 carries a reference device 4 in his/her mouth, the three-dimensional position of which is monitored during the whole image acquisition process by means of three cameras 5.

As can be seen from FIG. 2, the three cameras 5 are connected to a 3-D detection unit 6. Tomograph 1 and 3-D detection unit 6 are connected to a processing unit 7, which assembles the scans from the tomograph into a three dimensional image.

As shown in FIGS. 3–5, reference device 4 consists of a mouth piece 10 and a reference member 11. The mouth piece 10 comprises a U-shaped bite-down plate 12 connected to an L-shaped arm 13. A attachment bracket 14 is connected to arm 13 by means of two screws 15. Bracket 14 carries a rod 16 of reference member 11. Rod 16 is rotatably held in bracket 14 and can be fixed against rotation by means of two screws 17. This provides the possibility to use any scanning plane of the imaging system, such as coronal or sagittal scanning. Two lateral bodies 18 are arranged at the ends of rod 16, each carrying two fingers 19.

Fourteen infrared diodes are mounted to the lateral bodies 18 and the fingers 19. They are used as reference markers and their position can be measured by the cameras 5 and the 3-D detection unit 6. For this purpose, the diodes 20 are connected to 3-D detection unit 6 by means of cables 21 and are driven in multiplexed operation.

As can be seen from FIG. 5, the lateral bodies 18 are slightly inclined in respect to rod 16 such that not all of the diodes are arranged in the same plane. This increases the accuracy of the measured position of reference device 4.

Reference points 23 consisting of a material that can be detected by tomograph 1 are attached to the lateral bodies 18. Different positions are used to arrange the reference points 23 and the diodes 20 on the lateral bodies. The function of the reference points 23 is described below.

The apparatus works as follows:

Before image data acquisition, bite-down plate 12 is embedded in rapidly settling dental impression material and introduced into the patient's mouth. The patient bites bite-down plate 12 until the material is hardened. This provides a substantially rigid connection between reference device 4 and the teeth of the patient's upper jaw and thereby between reference device 4 and the patient's skull. A further connection between the reference device and the patient's head is not required.

Then rod 16 is positioned in bracket 14 in a position where the diodes 20 can be detected by the cameras 5 during the whole tomographic measurement. At least three diodes should be visible. The rod 16 is fastened by means of screws 15.

Now the patient is introduced into tomograph 1 and a plurality of conventionally scanned sectional images are acquired. For each scanned image, the position of the diodes and thereby the three dimensional orientation of reference device 4 relative to the camera system is measured.

The positions of both lateral bodies 18 can be measured independently for detecting a relative movement of the lateral bodies 18 and thereby a deformation of the geometry of reference device 4.

Furthermore, the movement of the table carrying the patient can be determined by infrared diodes 8. (FIG. 2).

In addition to this, at least one image is acquired showing at least three or more of the reference points 23.

This provides the following data:

1. All scanned images that show the reference points 23 allow the determination of the position of the scanning plans of the imaging system in respect to the camera system, i.e. the relation of the coordinate system of tomograph 1 in respect to the coordinate system of 3-D detection unit 6. (Alternatively, the position of the scanning plane of the imaging system in respect to the camera system may also be known from an earlier calibration, in which case the reference points 23 are not required).

2. As mentioned above, the 3-D position of reference device 4 is recorded for each sectional image scanned by the tomograph. This makes it possible to calculate all translatory and rotatory movements of the patient in respect to the coordinate system of the tomograph, i.e. the relative position of the patient's head in respect to the tomograph is known. The corresponding information is stored for each scanned image.

The information stored under point 2 allows 3-D processing unit 7 to assemble the sectional images into a high quality and precise three dimensional image taking account of the patient's head movements.

The three dimensional image is stored together with information describing the relative position of reference device 4 in respect to the three dimensional image (i.e. indicating the relative position of reference device 4 in respect to the patient's head).

After the measurement, reference device 4 is removed from the patient's teeth. However, as long as the hardened impression material remains on the bite-down plate, the reference device can always be attached in the same position on the teeth of the patient's upper jaw. Since information indicating the relative position of reference device 4 in respect to the coordinate system of the 3-D image has been stored together with the 3-D image, the position of the patient's head can immediately be determined when the reference device is reattached. This can e.g. be used when the patient has to undergo surgical treatment several days after image data acquisition. The reference device is again inserted into the patient's mouth and the surgeon's 3-D detection system can determine its position. The same 3-D detection system can e.g. also be used for measuring the position of surgical instruments and for overlaying them with the 3-D image of the patient's head.

Preferably, mouth piece 10 and reference member 11 can be separated from each other such that after establishing the tomographic image reference number 11 can be used for other patients. The mouth piece adapted to the patient is retained and can be reconnected to the reference member during later surgical treatment. For this purpose, the parts are designed such that the relative position between reference member 11 and mouth piece 10 can be re-established accurately.

The concept described here allows the generation of three-dimensional images having high accuracy while it obviates the need to immobilize the position of the head (or any other body part) during image acquisition and surgical treatment. By means of continuous measurement of the head position during acquisition, movements of the patient can be compensated for.

In addition to the infrared diodes mentioned above, a further set of diodes 9 (FIG. 2) can be attached to the tomograph for making the scanning plane and for determination of its position. They can be used for measuring the inclination of the tomograph and/or for determining the relative position between cameras and the tomograph (i.e. the relation between the coordinate systems of the 3-D detection unit and the tomograph).

The basic concept can also be embodied using means different from those described so far. For example, it is possible to vary the design of reference device 4. Depending on desired accuracy of the 3-D detection unit, reference device 4 can be more compact and e.g. have the shape of a baby's comforter, which is attached to one or more teeth of the upper jaw.

Instead of using dental impression material for attaching the reference device, suitable clamps or other means, such as dental prostheses, can be used.

In the present embodiment, the position of reference device 4 is determined from the position of the diodes 20. It is conceivable, however, that no active components are arranged on reference device 4 and its position is determined by processing the images from the cameras 5. The position of the head can also be measured directly, without using reference device 4, by recording it using several cameras and calculating its position by image processing.

Determining the position by optical means is preferred because optical signals do not interfere with the operation of the tomograph. Furthermore, it is fast and e.g. allows to detect a movement during acquiring a single sectional image in a short time interval—if necessary, the scanned image can be corrected in its position and/or be re-scanned.

It is, however, possible to perform a position measurement based on non-optical methods, such as ultrasound triangulation or radio-triangulation.

In the present embodiment the invention is applied for a computer tomograph, but it can also be used in other 3-D imaging techniques of body parts, e.g. in NMR tomography, ultrasound scanning techniques, angiography, positron emission tomography, imaging nuclear medical methods, planar radiography etc.

In all these cases, the tomograph (the image acquisition device) forms a first detector, which is acquiring single scans during an extended time interval, from which scans the complete three dimensional images can be assembled. At the same time, as second detector, independent of the first detector, is used for continuously measuring and recording the position of the head (or any other body part to be viewed). The positional data retrieved in this way are used for correcting (if necessary) the data from the first detector and for generating the three dimensional image.

What is claimed is:

1. A method for recording a three dimensional image of a part of a patient's body, wherein a plurality of individual scans acquired by first detector (1) is assembled to the three dimensional image, the method comprising the steps of: characterized in that during acquiring said scans movement of the part of the body are detected by at least 1 second detector (5,6); storing of position information of said part of said body corresponding to each of the acquired scans; and compensating for the detected movements using said positional information when assembling the individual scans.

2. The method of claim 1, characterised in that the movements are detected optically.

3. The method of one of the preceding claims characterised in that reference markers (20) are connected to the part of the body and that the position of the reference markers is detected by the second detector (5).

4. The method of claim 3, characterised in that the reference markers (20) are mounted to a reference device (4), which is mounted to the part of the body.

5. The method of claim 4, characterised in that the part of the body is a head and that the reference device (4) is mounted to at least one tooth or tooth replacement of the upper jaw and, preferably, to no further parts of the head.

6. The method of one of the claims 4 or 5, characterised in at least three marks (23) detectable by the first detector (1) are arranged on the reference device (4), which marks (23) are used for determining the relative position between the first (1) and the second (5,6) detector.

7. The method of one of the claims 3–6, characterised in that information defining the positional relation of the reference markers (20) to the part of the body are stored together with the three-dimensional image.

8. The method of one of the preceding claims characterised in that the first detector (1) is a tomograph, preferably a NMR- or X-ray-tomograph, especially a computer tomograph.

9. The method of claim 8, charaterised in that the patient is resting on a table, the movement of which table is recorded.

10. An apparatus for recording a three dimensional image of a part of patient's body by means of a first detector (1) for acquiring individual scans of the part of the body, the apparatus comprising: a processing unit (7) for assembling the individual scans to the three dimensional image; characterized in that a second detector (5,6) for measuring changes in the position in the part of the body while acquiring the individual scans; and position information storage for recording said changes in said position of each of the individual scans, wherein the positional information of the second detector (5,6) are fed to the processing unit (7).

11. The apparatus of claim 10, characterized in that the second detector (5,6) comprises optical detectors.

12. The apparatus of one of the claims 10 or 11, characterised by a table measuring unit for detecting a movement of a table of the apparatus.

13. The apparatus of one of the claims 10 or 12, charaterised in that it comprises markers (9) mounted in defined relation to the first detector (1), the position of which markers is detectable by the second detector for determining the relative position between the first and second detectors.

14. A reference device for being mounted to a head while acquiring a three-dimensional image of the head, characterised by a mouth piece (10) suited for mounting the reference device to at least one tooth of the upper jaw, to a tooth replacement or to a dental prosthesis, and further characterised by a reference member (1) suited for being detected by a position measuring system, wherein the reference member (11) is tiltable in respect to the mouth piece (10).

15. The apparatus of claim 11, characterized in that the optical detectors are several cameras (5).

16. The apparatus of claim 11, characterized in that the first detector (1) is a tomograph selected from the group comprising NMR-, X-Ray-, and computer tomograph.

17. A reference device according to claim 14, wherein the tiltable reference member (11) facilitates the establishment of a selected orientation for each recording geometry.

18. A reference device according to claim 17 further comprising diodes (20) and reference points (23) positioned at different locations.

19. A reference device according to claim 17 further including a pair of bodies (18) of said reference member (11) that can be monitored independently for detecting a relative movement of the bodies (18).

20. A reference device according to claim 19, wherein a deformation of a geometry of said reference device (11) is determined by said relative movement.

21. An apparatus for recording a three dimensional image of a part of a patient's body by means of a first detector (1) for acquiring individual scans of the part of the body, comprising a processing unit (7) for assembling the individual scans to the three dimensional image, characterized by a second detector (5,6) for measuring changes in the position of the part of the body while acquiring the individual scans, wherein results of the second detector (5,6) are fed to the processing unit (7), said apparatus further comprising markers (9) mounted in defined relation to the first detector (1), the position of the markers is detectable by the second detector (5,6) for determining the relative position between the first and second detectors.

* * * * *